United States Patent [19]

Johnston

[11] Patent Number: 4,764,013

[45] Date of Patent: Aug. 16, 1988

[54] INTERFEROMETRIC APPARATUS AND METHOD FOR DETECTION AND CHARACTERIZATION OF PARTICLES USING LIGHT SCATTERED THEREFROM

[75] Inventor: Roger G. Johnston, Los Alamos, N. Mex.

[73] Assignee: The United States of America as represented by the United States Department of Energy, Washington, D.C.

[21] Appl. No.: 28,987

[22] Filed: Mar. 23, 1987

[51] Int. Cl.$^4$ ................................................ G01B 9/02
[52] U.S. Cl. .................................... 356/349; 356/338; 356/340; 356/364
[58] Field of Search ............... 356/336, 338, 340, 364, 356/368, 349; 250/225

[56] References Cited

U.S. PATENT DOCUMENTS 3,612,688 10/1921 Liskowitz ..................... 356/364 X
4,306,809 12/1981 Azzam ............................... 356/368

OTHER PUBLICATIONS

Hunt et al., "A Polarization-Modulated Light Scattering Instrument for Determining Liquid Aerosol Properties", *Proc Ico Conf. Methods in Sci. and Incl. Meas.*, Tokyo, 1974, pp. 435-410.
Bickel et al., "Application of Polarization Effects in Light Scattering: A New Biophysical Tool", *Proc. Natl. Acad. Sci., USA*, vol. 25, No. 2, pp. 486-490, 2/76.
Roger G. Johnston et al., "Phase Differential Scattering from Microspheres", Appl. Opt. 25, 3566-3572 (Oct. 1986).

*Primary Examiner*—Davis L. Willis
*Assistant Examiner*—Matthew W. Koren
*Attorney, Agent, or Firm*—Milton D. Wyrick; Samuel M. Freund; Judson R. Hightower

[57] ABSTRACT

Interferometric apparatus and method for detection and characterization of particles using light scattered therefrom. Differential phase measurements on scattered light from particles are possible using the two-frequency Zeeman effect laser which emits two frequencies of radiation 250 kHz apart. Excellent discrimination and reproducibility for various pure pollen and bacterial samples in suspension have been observed with a single polarization element. Additionally, a 250 kHz beat frequency was recorded from an individual particle traversing the focused output from the laser in a flow cytometer.

51 Claims, 13 Drawing Sheets

4,764,013

INTERFEROMETRIC APPARATUS AND METHOD FOR DETECTION AND CHARACTERIZATION OF PARTICLES USING LIGHT SCATTERED THEREFROM

BACKGROUND OF THE INVENTION

The present invention relates in general to particle detection by light scattering techniques and, more particularly, to the characterization of particles by observing the phase and amplitude of the beat frequency resulting from the interference of the light scattered as a result of the interaction of two collinear, orthogonally polarized light beams having a small difference in wavelength with the particles under investigation as a function of scattering angle. This invention is the result of a contract with the Department of Energy (Contract No. W-7405-ENG-36).

Phase and polarization properties of elastically scattered light have received increased attention in recent years since they provide more information about the size, morphology, optical activity, and internal structure of the scattering particle than do nonpolarization measurements of the scattered irradiance. The Mueller scattering matrix is commonly used to characterize elastic light scattering from particles. The 16 real elements of this matrix specify the intensity and polarization of the scattered light. Although only the irradiances of various polarizations need be measured in experiments designed to determine individual Mueller matrix elements it is difficult to separate, as a practical matter, contributions from other Mueller matrix elements to the element under investigation. Wavelength and angular parameterization of the Mueller matrix elements can, in select situations, provide a significant amount of information about the scattering particle or particles.

The amplitude scattering matrix, by contrast, has received little attention since it explicitly relates the phases of the incident and scattered electric fields. Experimental phase measurements have traditionally proven to be difficult since interferometric techniques are required.

Two-frequency Zeeman effect lasers and frequency-stabilized lasers have recently become available commercially. As a result, certain types of phase information in the scattered light are now readily accessible. When the orthogonally polarized, binary output radiation from such a device is scattered by a sample of particles or a single particle of interest in a flow, and the resulting two scattered frequencies are made to interfere on a photodetector, after passing through a polarization element, the phase and amplitude of the resulting beat frequency contains useful information concerning the nature of the scattering particles. The term, phase differential scattering, PDS, will be used to refer to the phase and amplitude measurements made when a sample of particles in a flow or individual particles scatter orthogonally polarized, two-frequency electromagnetic radiation. Phase differential scattering is sensitve to three scattering mechanisms, each of which depends upon the nature of the scatterer. All three mechanisms may occur simultaneously from a single scattering particle. At a given scattering angle, the scattering particle may scatter the two incident radiations with different efficiencies. This can be measured by setting the transmission axis of the analyzing polarizer at 45° to the horizontal and recording the amplitude of the beat frequency between the two wavelengths of the radiations. The scattering particle may also retard one of the two scattered radiations relative to the other. This phenomenon manifests itself in the phase of the beat frequency when the analyzing polarizer is oriented at 45°. The scatterer may also partially convert one orthogonal polarization of the radiations into the other. The extent and relative retardation of this "mixing" of polarizations depends upon the asymmetry of the particles. It can be characterized by measuring the amplitude and phase, respectively, of the beat frequency when the analyzing polarizer is set to 0° and 90°.

Accordingly, it is an object of the present invention to provide an apparatus and method for accessing much of the information contained in the Mueller scattering matrix or theoretically available from conventional interferometric measurements on light scattered from a sample of particles or from individual particles under investigation.

Another object of our invention is to provide an apparatus and method for identifying and characterizing particles in samples.

Yet another object of the subject invention is to provide an apparatus and method for identifying and characterizing individual particles in a flowing system.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the the present invention, as embodied and broadly described herein, the apparatus of this invention includes a means for producing a first radiation having a first wavelength and a first polarization and a means for producing a second radiation substantially collinear with the first radiation having a second polarization substantially orthogonal to the first polarization, containment means containing a sample of particles to be identified and characterized for allowing the first and second radiations to scatter from collisions with the particles in the sample, and for allowing scattered first and second radiations to emerge from the containment means; polarization means receive the scattered first and second radiations and resolve the scattered first and second radiations, the polarizations means having an axis of transmission along which the resolved scattered first and second radiations pass; photodetector means receive the resolved scattered first and second radiations and detect the resolved first and second radiations and output the beat frequency having a relative phase and amplitude resulting from the interaction between the resolved scattered first and second radiation; and measurement means receive the beat frequency in order to measure the relative phase of the beat frequency and to output the relative phase for use in identifying and characterizing the particles.

In a further aspect of the present invention, and in accordance with its objects and purposes, a method for identifying and characterizing particles in a sample includes the steps of producing a first radiation having a first wavelength and a first polarization; producing a second radiation substantially collinear with said first radiation having a second wavelength and a second polarization substantially orthogonal to the first polarization; scattering the first and second radiations by irradiating the sample with the first and second radiations; receiving and resolving the scattered first and second radiations along an axis of transmission having a predetermined polarization angle, and outputting resolved scattered first and second radiations; detecting the resolved scattered first and second radiations, the detection producing a beat frequency having a relative phase and amplitude from the interaction of the resolved scattered first and second radiations, and outputting the beat frequency; measuring the relative phase of the beat frequency; and finally outputting the relative phase.

In a still further aspect of the present invention, and in accordance with its objects and purposes apparatus is provided for the identification and characterization of individual particles in a flow by observing the light scattered therefrom, comprising in combination means for producing a first radiation having a first wavelength and a first polarization; means for producing a second radiation substantially collinear with the first radiation having a second wavelength and a second polarization substantially orthogonal to the first polarization; containment means controlling the flow of the individual particles for allowing the first and second wavelengths to scatter from collisions with the individual particles; polarization means receiving the scattered first and second radiations for resolving the scattered first and secnd radiations, the polarization means having an axis of transmission along which resolved scattered first and second radiations pass; photodetector means receiving and detecting the resolved scattered first and second radiations for outputting a beat frequency, having a relative phase and amplitude, resulting from interaction between the resolved scattered first and second radiations; and measurement means receiving the beat frequency for measuring and outputting the relative phase of said beat frequency as a function of time.

In a still further aspect of the present invention, and in accordance with its objects and purposes, the method of indentifying and characterizing individual particles in a flow by observing light scattered therefrom comprises the steps of producing a first radiation having a first wavelength and a first polarization; producing a second radiation substantially collinear with the first radiation having a second wavelength and a second polarization substantially orthogonal to the first polarization; scattering the first and second radiations by irradiating the particles in the flow with the first and second radiations; receiving and resolving the scattered first and second radiations along an axis of transmission having a predetermined polarization angle, and outputting resolved scattered first and second radiations; detecting the resolved first and second radiations, the detection producing a beat frequency having a relative phase and amplitude from the interaction of the resolved scattered first radiation with said resolved second scattered radiation, and outputting the beat frequency; measuring the relative phase of the beat frequency as a function of time; and outputting the relative phase as a function of time.

BRIEF DESCRIPTION OF THE DRAWINGS

The accompanying drawings, which are incorpoated in and form a part of the specification, illustrate two embodiments of the present invention and, together with the description, serve to explain the principles of the invention. In the drawings.

DETAILED DESCRIPTION OF THE INVENTION

Figure 1:
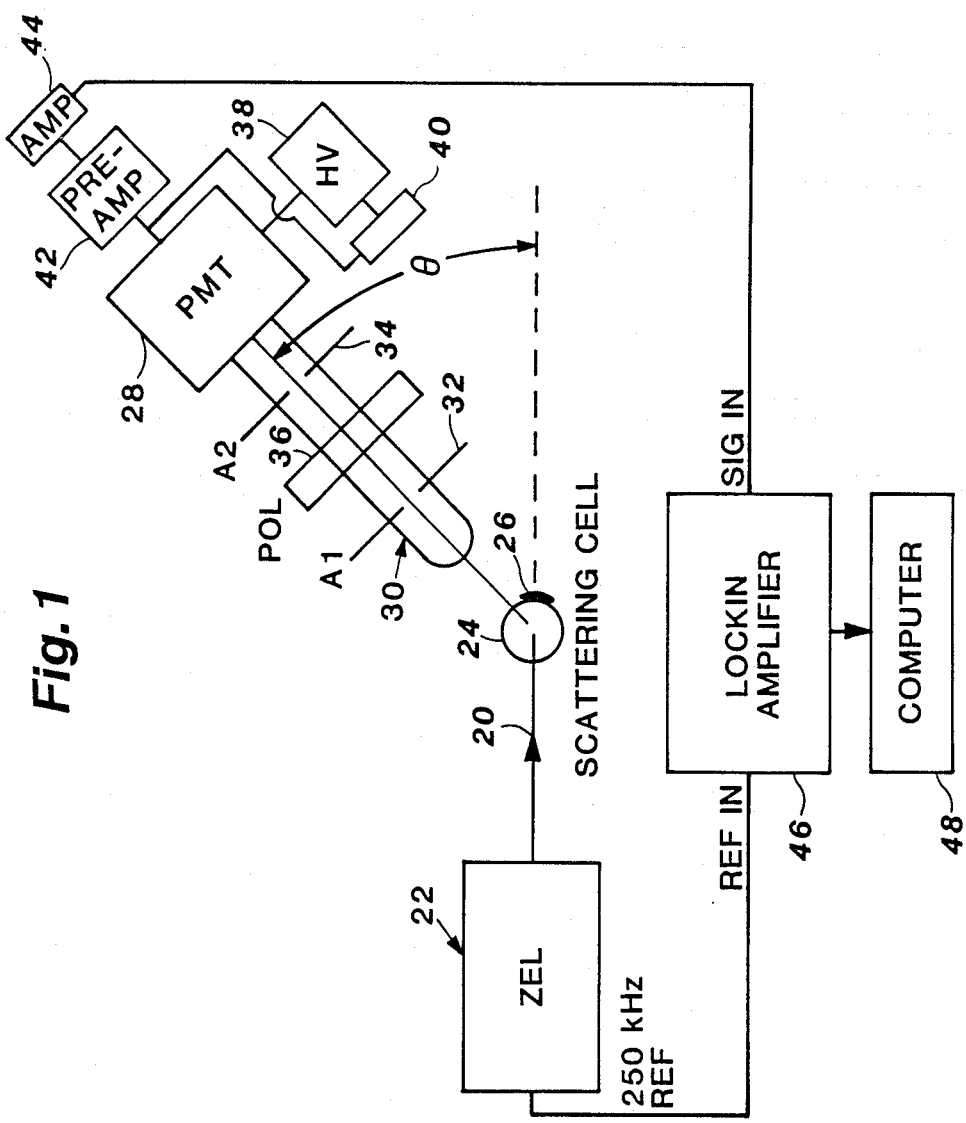
FIG. 1 is a schematic representation of the aparatus of the subject invention showing the two-frequency laser, the scattering cell, the linear or circular polarization analyzer, the photomultiplier detector, and associated electronics. Two apertures are also shown for defining the scattering volume. The phase and amplitude of the beat frequency are measured with the lock in amplifier.

Briefly, the subject invention is an apparatus and method for obtaining significantly more information about a scattering particle than conventional nonpolarized scattering irradiance measurements permit, while being simpler and freer from artifacts than other advanced scattering procedures such as Mueller matrix measurements or those involving optical heterodyning. The recent commercial availability of two-frequency Zeeman effect lasers makes phase differential scattering, which is the basis for the present invention, practical. This laser uses the Zeeman effect to generate two coherent, collinear laser beams having orthogonal polarizations and a frequency difference of only 250 kHz. The frequency difference is stable to at least 0.1 parts per million. The polarizations may be linear or circular. When the two collinear laser beams, which need not be focused are allowed to enter a cell or cuvette containing the sample of interest, the impinging radiation is elastically scattered from the particles therein, and the scattered radiation allowed to interfere on a photodetector, a 250 kHz beat frequency results. The relative phase of this beat frequency depends on the optical phase difference between the two scattered radiations. The relative phase and amplitude of this beat frequency contains the phase differential scattering information of interest. Additional information is available if the scattered radiation is investigated as a function of the scattering angle. Before reaching the photodetector the scattered light must pass through an analyzing polarizer and an aperture which defines the scattering volume. The angle of the polarization element's transmission axis (0°, 45°, or 90°) determines the nature of the recorded information. The phase of the beat frequency is compared with a 250 kHz reference sine wave generated within the Zeeman effect laser device. Individual particles passing through the laser beam may be investigated using substantially the same apparatus if the time dependence of the amplitude or phase of the beat signal is recorded. In this case it is advantageous to focus the output from the Zeeman effect laser in order to investigate only the desired particle and to increase incident radiation An excellent reference describing the interacting of light with small particles is, *Absorption and Scattering of Light by Small Particles*, by C. F. Bohren and D. R. Huffman (Wiley, New York, 1983). The nature of the structural information obtained from phase differential scattering can be determined from the scattering amplitude matrix formalism for light scattering. This matrix consists of four complex matrix elements and relates the incident and scattered electric fields. The values of these matrix elements depend on the size, morphology, optical activity, and internal structure of the scatterer. After light scattered by the particles of interest is directed through an analyzing polarizer the scattered intensity, I, at a photodetector has the form:

$$I = DC + \Gamma \cos(\Delta\omega t + \gamma), \quad (1)$$

where DC is a time-independent constant, $\Delta\omega = \omega_1 - \omega_2$, the difference between the two output frequencies of the Zeeman effect laser, and $\Gamma$ and $\gamma$ are the amplitude and phase, respectively, of the beat frequency. The phase differential scattering phase, $\gamma$, of Equation 1 can be related to the amplitude scattering matrix elements in various linear combinations for analyzing polarizer orientations of 0°, 45°, and 90°, which means that the measured phase shift should bear the signature of the scattering particles. Additonal information may be derived by determining the phase shift as a function of scattering angle as well as of the orientation of the analyzing polarizer. The amplitude, $\Gamma$, of the beat frequency can also be related to the scattering matrix elements. Moreover, both $\gamma$ and $\Gamma$ can be expressed as functions of Mueller scattering matrix elements. Expressions for $\gamma$ and $\Gamma$ can also be derived for the situations where the analyzing polarizer is a circular polarizer and/or the incident radiation is circularly polarized instead of being linearly polarized. To calculate scattering from a collection of randomly oriented particles, rotatioal averaging of the scattering results is required. A more detailed discussion can be found in "Phase Differential Scattering From Microspheres." by Roger G. Johnston, shermila B. Singham and Gary C. Salzman, Appl. Opt. 25, 3566-3572 (1986), the disclosure thereof hereby being incorpoated by reference herein.

In the situation where it is desirable to analyze one flowing particle at a time instead of the averaged effect of a plurality of particles, the passage of the particle through the laser beam produces a polarization analyzed signal at the detector which as the form:

$$I = A(t)\sin(\Delta\omega t + \phi(t)), \quad (2)$$

where $\Delta\omega/2\pi = 250$ kHz and A(t) is the termporal convolution of the particle with the focused laser beam. If $\phi(t) << 1$, it can be shown that:

$$I \approx A(t)(1 + \phi(t))\cos(\Delta\omega t). \quad (3)$$

The signal has an amplitude modulation instead of a frequency or phase modulation as described in Equation 1, and the pulse height of the signals can be investigated using a waveform recorder or other device. The phase $\phi(t)$ may also be extracted from the signal even when $\phi(t)$ is not $<<1$ by using a waveform recorder to record the signal.

Reference will now be made in detail to one embodiment of the invention, an example of which is illustrated in the accompanying drawing. Similar and identical structure will be labeled throughout using the same numerical call-outs. Turning now to FIG. 1, where the apparatus of the subject invention is shown in schematic form, it is seen that the measurements can be performed with a simple apparatus. Substantially collinear, two-frequency, orthogonal polarization laser beams 20 from Zeeman effect laser 22 are directed into a 4.70 cm diameter cylindrical borosilicate glass scattering cell 24 containing the sample under investigation suspended in a liquid medium. Typically, the sample is ultrasonically agitated for several minutes prior to use to reduce particle clumping. However, this type of agitation can damage bacteria and was not used for such particles. Unscattered light exiting the cell at 0° scattering angle is prevented from reflecting back into the scattering volume by an ultraflat black absorbing paint 26 disposed on the inner and outer surfaces of cell 24. Light scattered from cell 24 at nonzero scattering angles, $\theta$, is measured using a photomultiplier tube (PMT) 28 which is mounted on an arm 30 which rotates under computer control about the scattering cell. Before reaching PMT 28, the scattered light is passed through two 4 mm diameter apertures 32, 34 and a calcite polarizer 36 also mounted on arm 30. In one arrangement of the apparatus of the present invention, apertures 32, 34 and polarizer 36 are located at 14, 47, and 24.5 cm, respectively, from the center of the scattering cell. The angular width of aperture 34 is therefore approximately 0.5° as viewed from the center of the scattering cell. Apertures 32, 34 restrict the size of the scattering volume viewed by the photomultiplier tube and prevent the PMT 28 from "seeing" the cell walls at the points where the laser radiation enters and exits scattering cell 24. Apertures 32, 34 cause the scattering volume to be about 7.4 mm wide when viewed at $\theta=90°$. The scattered light at any chosen $\theta$, however, is not collected with equal efficiency from all portions of the scattering volume. Principally due to geometrical considerations, the majority of the scattered light is collected from a scattering volume only about 4 mm wide, as viewed at $\theta=90°$.

The polarizer 36 permits the parallel and perpendicular components of the electric field of the scattered radiation to interfere on PMT 28 so that the 250 kHz beat frequency can be detected. The transmission axis of polarizer 36 is oriented at an angle of 45° to the scattering plane. As is apparent from the discussion set forth hereinabove, other polarizer angles are appropriate for phase differential scattering measurements on optically active or nonspherical scatteres as well. The high voltage supplied to the PMT 28 by high voltage supply 38 was controlled by servo circuit 40 in order to maintain an approximately constant current at the photocathode thereof. This is required since the total scattered light intensity can vary over several orders of magnitude as a function of $\theta$. The output of PMt 28 is directed to a transimpedance preamplifier 42, the output of which is directed to a second amplifier 44. Preamplifier 42 and amplifier 44 have bandwidths of 300 kHz and 3 MHz, respectively. The output from amplifier 44 is directed to a phase-sensitive detector 46. Amplifier 44 has been found not to be required for strong scatteres. A typical time constant is 300 ms. The 250 kHz reference sine wave for the phase-sensitive detector derives from circuitry with the Zeeman effect laser and has a phase equal to the optical phase difference between the perpendicular and parallel electric fields generated by laser 22. Phase sensitive detector 46 is controlled and read by computer 48. For each sample, the phase of the 250 kHz beat frequency is recorded between 2 and 7 times for every scattering angle between 7° and 163° in steps of 1°. Test phase measurements were performed using function generators, comparisons with a commercial phase meter having an accuracy of about ±1°, and optical retardation tests. It is believed that the accuracy of phase sensitive detector 46 phase readings is ±0.5°. The reproducibility of these measurements was generally better than ±0.3°. Electronic phase shifts introduced by the components shown in FIG. 1 were found to be independent of the signal strength over the ranges observed.

Scattering cell 24 has a wall thickness of 2 mm and was slightly birefringent due to internal stresses in the glass. An approximate correction for this birefringence was applied to the phase differential scattering data at each scattering angle $\theta$ by subtracting the appropriate phase retardation of the scattered beam caused by the cell wall. This phase retardation is the change in the relative phases of the perpendicular and parallel components of the electric field when the cell wall is inserted into the path of the two-frequency laser. The measured values of the phase retardation for the cell wall varied from several tenths of a degree in magnitude to 1.7° as a function of $\theta$. These corrections are more difficult to perform and less accurate using other techniques.

Figure 2:
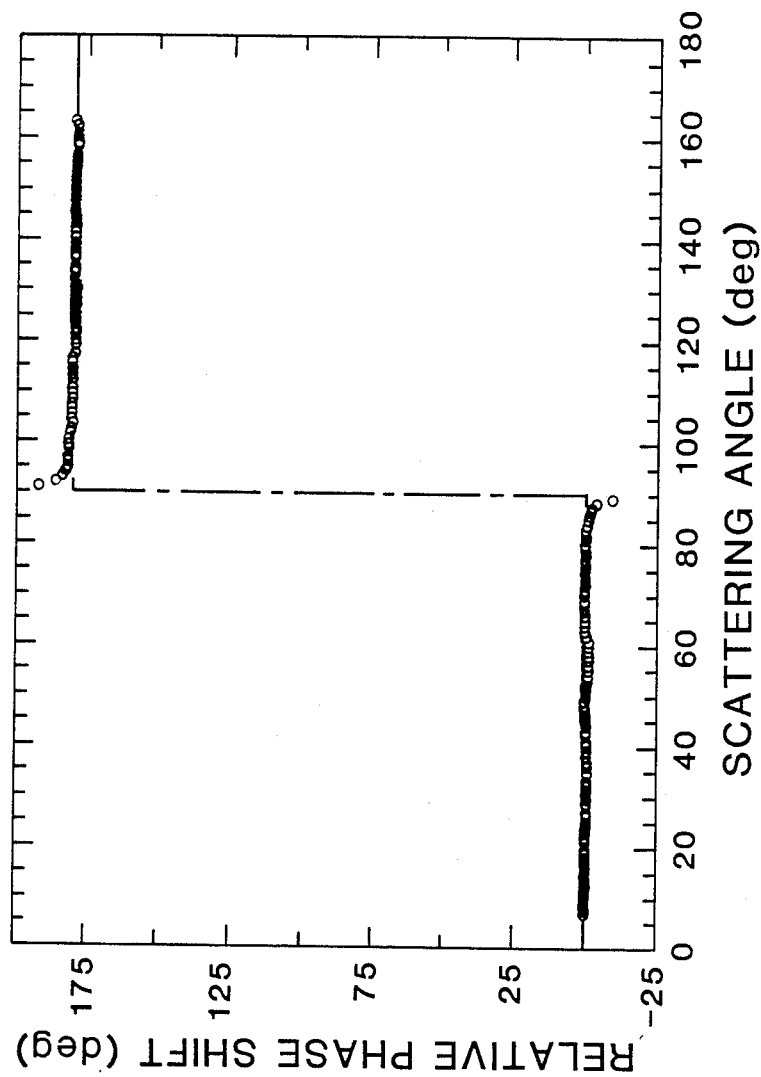
FIG. 2 shows the phase differential scattering ($\gamma$ versus $\theta$) for optically inactive 0.85 $\mu$m diameter polystyrene microspheres in a suspension having a concentration of $3.9 \times 10^{11}$/ml with the analyzing polarizer at 45°.

FIG. 2 shows the phase differential scattering signal $\gamma$ as a function of scattering angle $\theta$ for optically inactive polystyrene microspheres of 0.085 $\mu$m diameter. The circles represent data for an aqueous suspension of microspheres having a concentration of about $3.9 \times 10^{11}$ spheres/ml. The data were indistinguishable over two orders of magnitude in concentration. The theoretical curve (chain-dash) was calculated from Mie scattering theory. All data presented in graphic form herein is reported with respect to a value of $\gamma=0°$ at $\theta=90°$, as is appropriate for nonbirefringent samples. This was accomplished by measuring the phase of the 250 kHz beat frequency for light transmitted at $\theta=0°$ through the sample. The effects of any (constant) phase offset inherent in the detection electronics or the existence of a nonzero value for the relative phase difference between the two incident radiations are eliminated thereby. The reported values for $\gamma$ shown in FIG. 2 and elsewhere herein have also been corrected at each scattering angle for the retardation caused by the cell wall. This correction for the cell birefringence is an excellent approximation but it ignores the mixing of the 2 frequencies that will occur if the fast axis of the cell wall is not 0° to 90° to the parallel direction. For example, a cell wall with a birefringence of 2° will mix each pure frequency with between 0 and 1.7% of the other frequency depending on orientaton of the fast axis. An exact correction for the cell birefringence is possible if the two-frequency laser is used to measure the angle of the fast axis at each point of the cell wall. Since the frequency mixing due to the cell birefringence was found to be minimal, the exact correction was not used. When the polarizer in FIG. 1 was set at 0° or 90° to the scattering plane, the amplitude of the 250 kHz signal was too small to reproducibly record the phase as would be expected since the amplitude would, in fact, be zero for optically inactive perfect spheres for these polarization alignments.

It should be mentioned at this point that the experimental data shown in FIG. 2 and subsequent figures all reflect error bars which are too small to be resolved on the scale of the figures. The data points near 90°, however, can have uncertainties as large as ±5°. Moreover, although the microspheres are slightly polydispersive in that they possess a 0.0055 $\mu$m standard deviation in their diameters, the theory is approximately correct without taking this into consideration. The $\gamma$ versus $\theta$ behavior exhibited in the accompanying figures hereof is entirely a polarization effect and is unrelated to the slight $(3.3 \times 10^{-5}$ nm) difference in wavelength between the two laser lines. The phase shift $\gamma$ is zero for all scattering angles when the analyzing polarizer 36 of FIG. 1 hereof is placed in the incident beam between the laser and the scattering cell. Finally, the observed data were found to possess excellent reproducibility even when several hours separated the runs and the scattering cell was removed from the apparatus and repositioned for subsequent runs.

Figure 3:
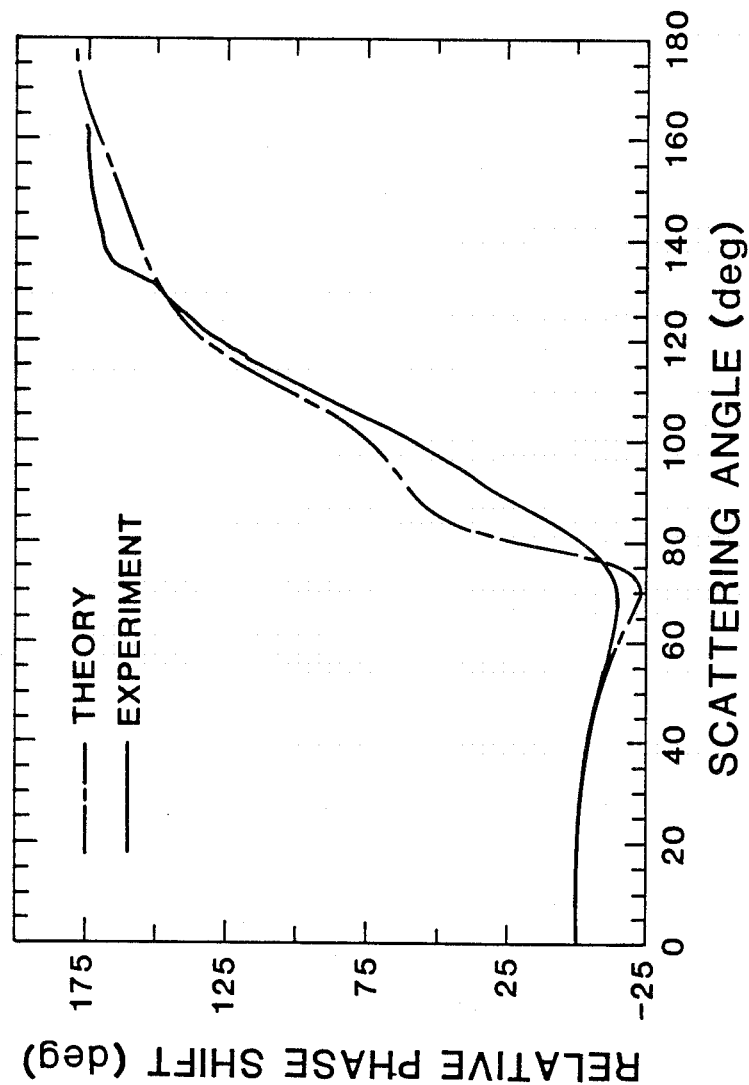
FIG. 3 shows the phase differential scattering for 0.482 $\mu$m diameter polystyrene microspheres in a suspension having a concentration of $1.4 \times 10^8$/ml.
Figure 4:
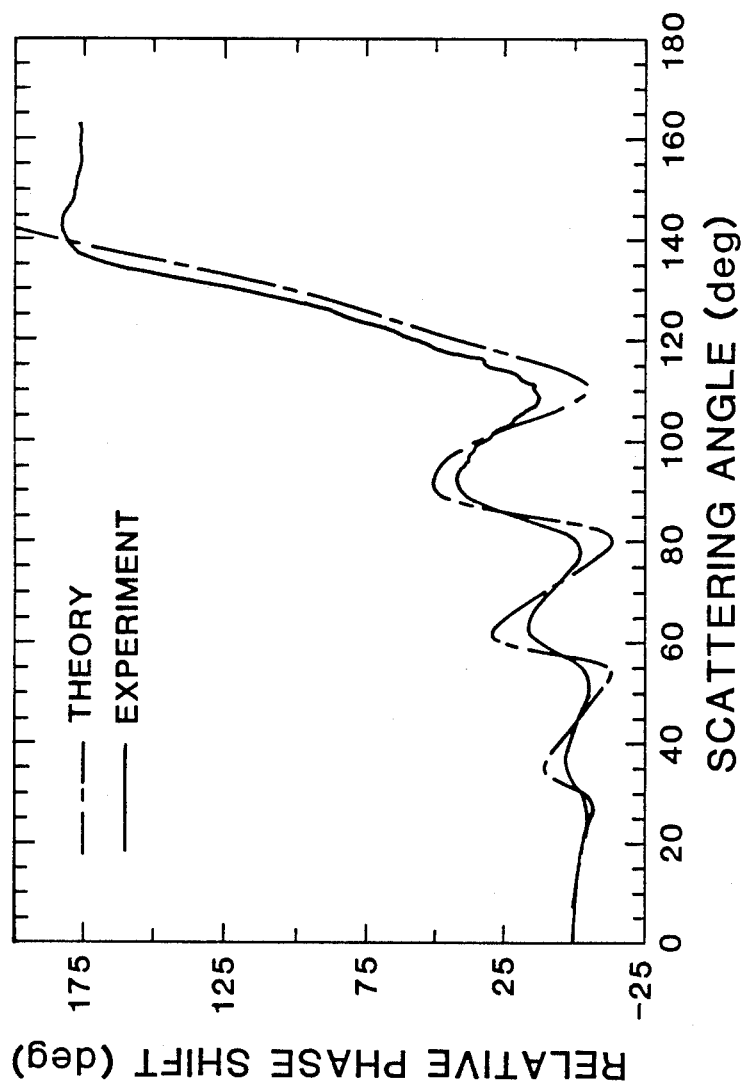
FIG. 4 shows the phase differential scattering for 1.088 $\mu$m polystyrene microspheres in a suspension having a concentration of $5.6 \times 10^7$/ml.

FIGS. 3 and 4 exhibit theoretical and experimental phase differential scattering results for increasing sizes of microspheres. FIG. 3 reflects phase differential scattering for 0.482 $\mu$m diameter polystyrene microspheres having a standard deviation of ±0.0259 $\mu$m at a concentration of $1.4 \times 10^8$/ml. Data were taken at every 1° of scattering angle. FIG. 4 represents phase differential scattering for 1.088 $\mu$m diameter polystyrene microspheres having a standard deviation of 0.079 $\mu$m at a concentration of $5.6 \times 10^7$/ml. It is also of interest that the fine structure observed in FIGS. 3 and 4 is far more detailed than that observed by the inventor for measurements of several Mueller matrix elements for spheres having the same size.

Figure 5:
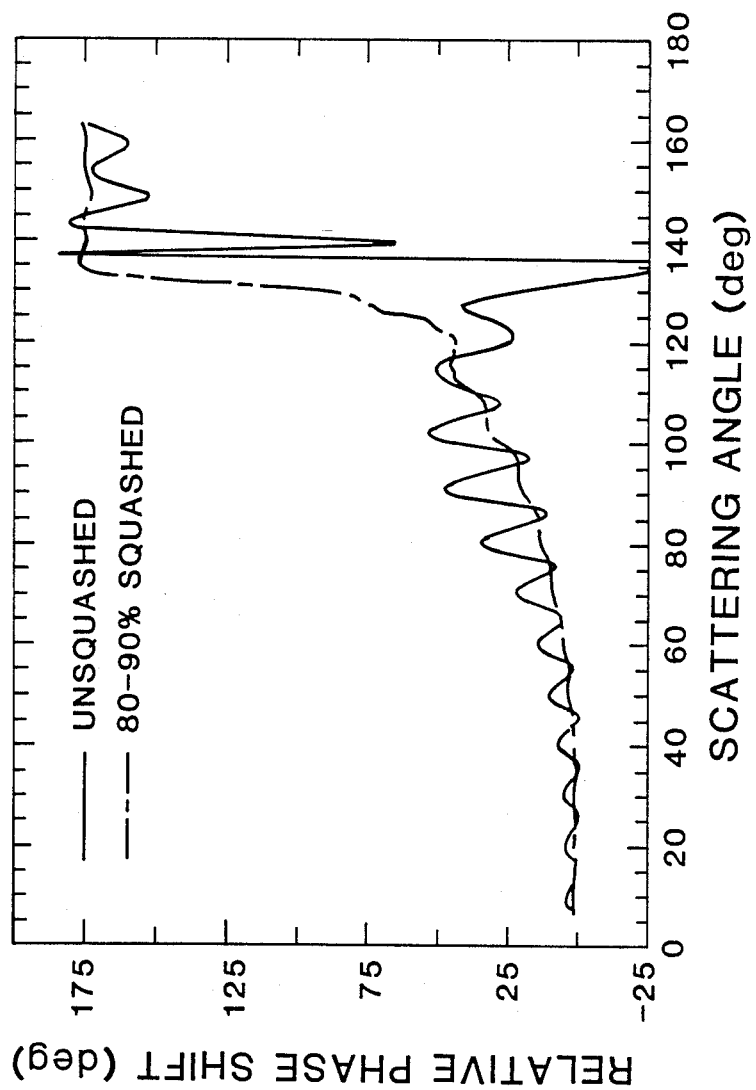
FIG. 5 shows the phase differential scattering for squashed and unsquashed 2.95 $\mu$m diameter polystyrene microspheres having a concentration of $1.1 \times 10^6$/ml total for squashed and unsquashed species. Between 80% and 90% of the squashed particles were nonspherical.

FIG. 5 demonstrates that the phase differential scattering signal depends strongly on the shape of the scattering particles. The solid curve represents the observed signal for regular 2.95 μm±0.13 μm diameter polystyrene microspheres having a concentration of $1.1\times10^6$/ml, while the chain-dash curve represents the same concentration of 2.95 μm microspheres, 80-90% of which having been squashed into nonshperical geometry as was observed using an optical microscope. The most common shapes were found to be disks and plano-concave or concave-convex geometries. The majority of the remaining 10-20% of the polystyrene microspheres were unaffected by the squashing process. There was little evidence of fragmented particles.

Figure 6:
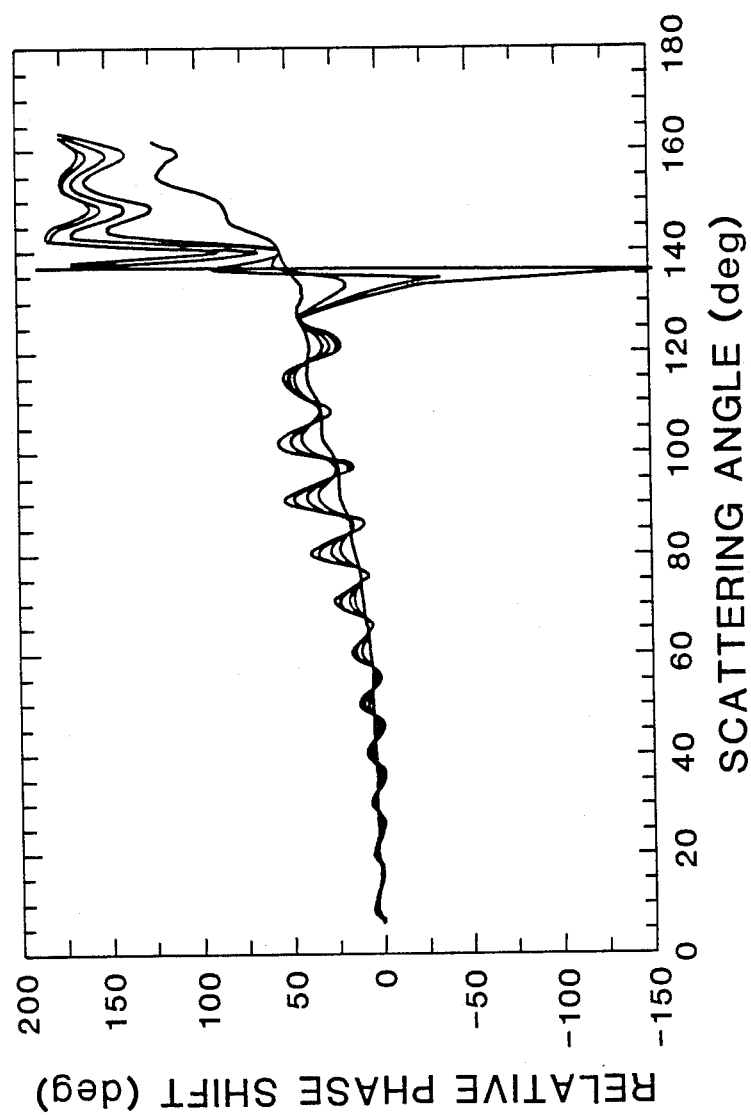
FIG. 6 shows the concentration dependence of the phase differential scattering for 2.95 $\mu$m diameter polystyrene microspheres. It is to be observed that the lower the concentration of spheres, the larger the amplitude of the ripples in the $\gamma$ versus $\theta$ curves. Suspension concentrations ranged from $5.3 \times 10^5$ml to $7.4 \times 10^6$/ml.

FIG. 6 shows the concentration dependence of the phase differential scattering signal on the concentration of scattering particles. Data shown are for sphere concentrations: $5.3\times10^5$/ml (top curve), and 1.1, 2.1, 3.7, and $7.4\times10^6$/ml (lowest curve). The lower the concentration the greater the amplitude of the $\gamma$ versus $\theta$ curves. However, the locations of the maxima and minima remain substantially unaffected by concentration. Although sample turbidities were low, it is believed by the inventor that multiple scattering is the likely mechanism for the concentration effect shown in FIG. 6 hereof.

FIGS. 7-11 hereof were obtained with the analyzing polarizer at 45° and all particles were suspended in water.

Figure 7:
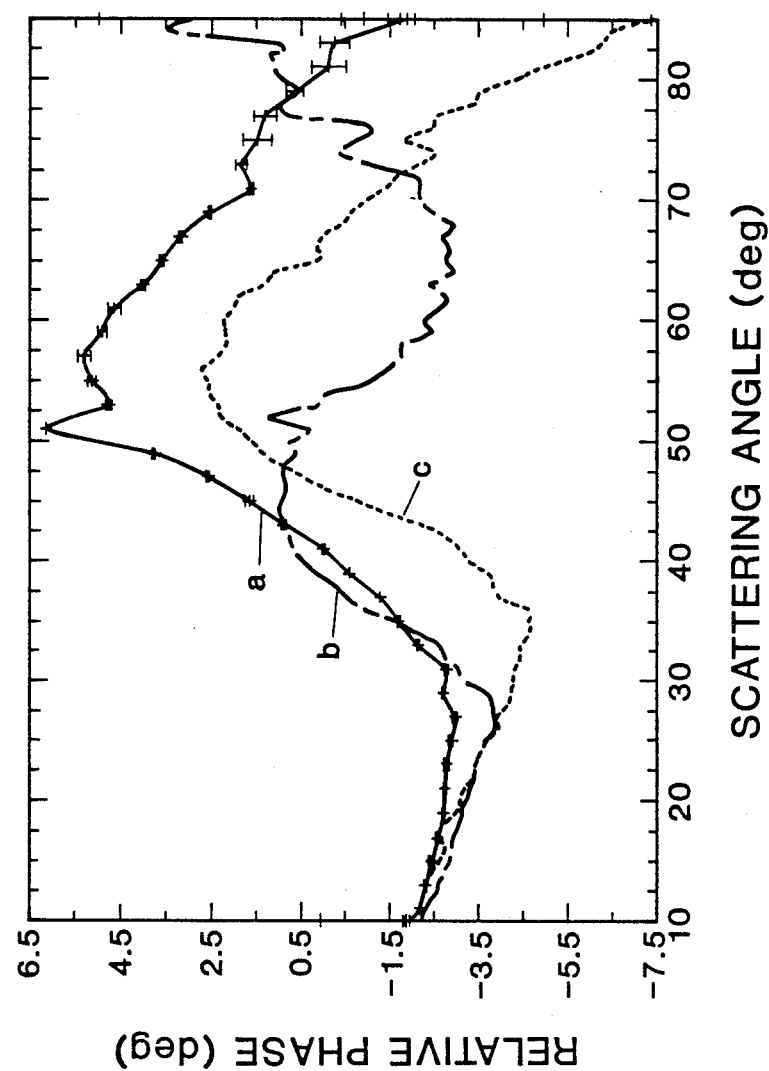
FIG. 7 shows the discrimination of the phase differential scattering spectrum for three bacterial specimens in suspensions having approximately $10^7$/ml concentration.
Figure 8:
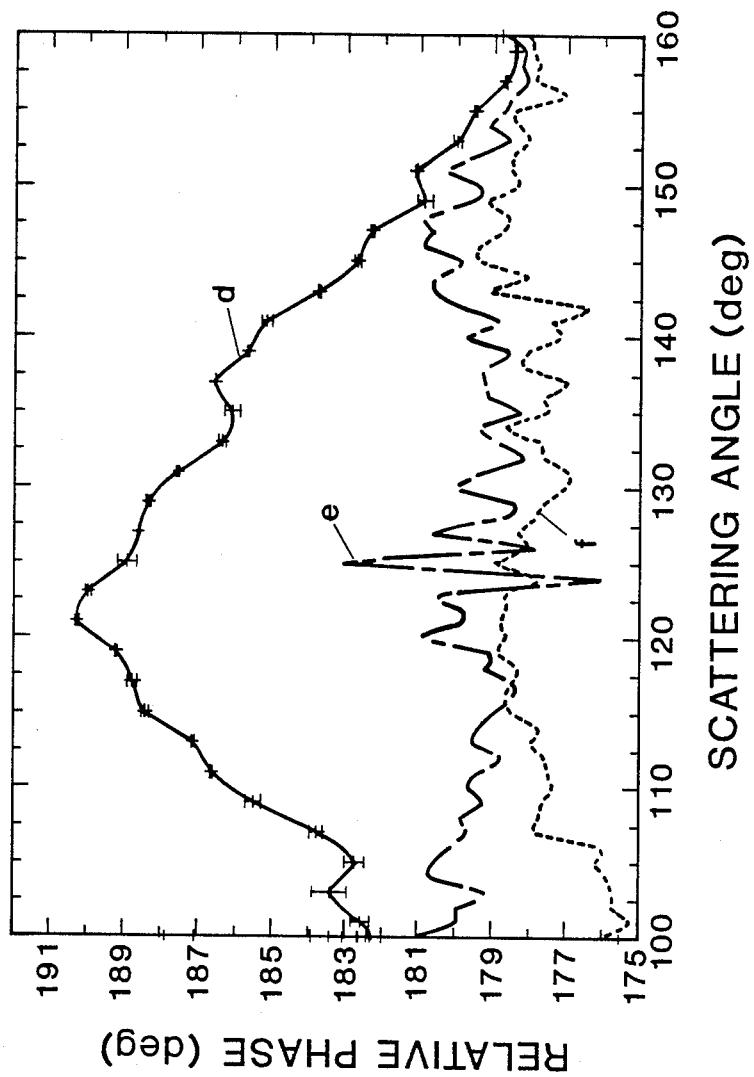
FIG. 8 shows a spectrum of the same three bacterial suspensions shown in FIG. 7 but with the phase differential scattering spectrum being extended to a 160° scattering angle.

FIGS. 7 and 8 show the observed phase discrimination among pure suspensions of bacteria at concentrations of approximately $1\times10^7$/ml at forward and backward scattering angles, respectively. Shown are the phase differential scattering signals for *V. fluvialis* (FIG. 7a and FIG. 8 at plot d), *N. lactamica* (FIG. 7 at plot b and FIG. 8 at plot e), and *B. subtillis* (FIG. 7 at plot c and FIG. 8 at plot f).

Figure 9:
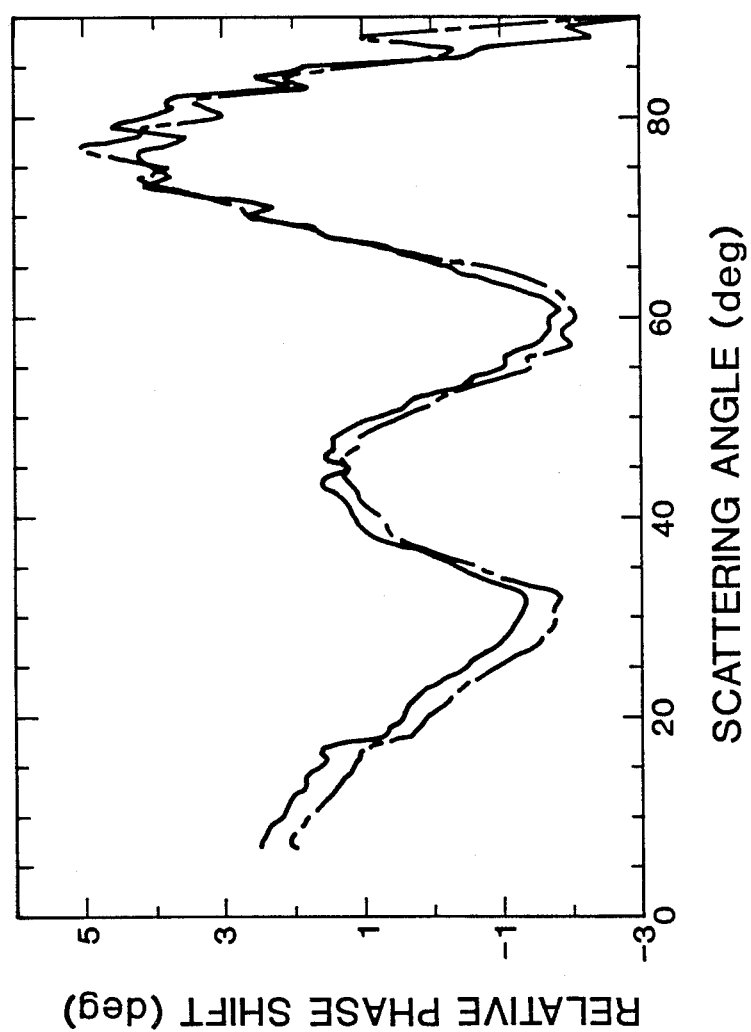
FIG. 9 shows the typical reproducibility for phase differential scattering experiments in aqueous suspensions of bacteria.

FIG. 9 shows the phase differential scattering signal for $5\times10^7$/ml of the bacteria *B. golbigii*. The two curves represent runs on the same sample taken three hours apart, the sample scattering cell and the phase differential scattering instrument itself having been adjusted between the runs.

Figure 10:
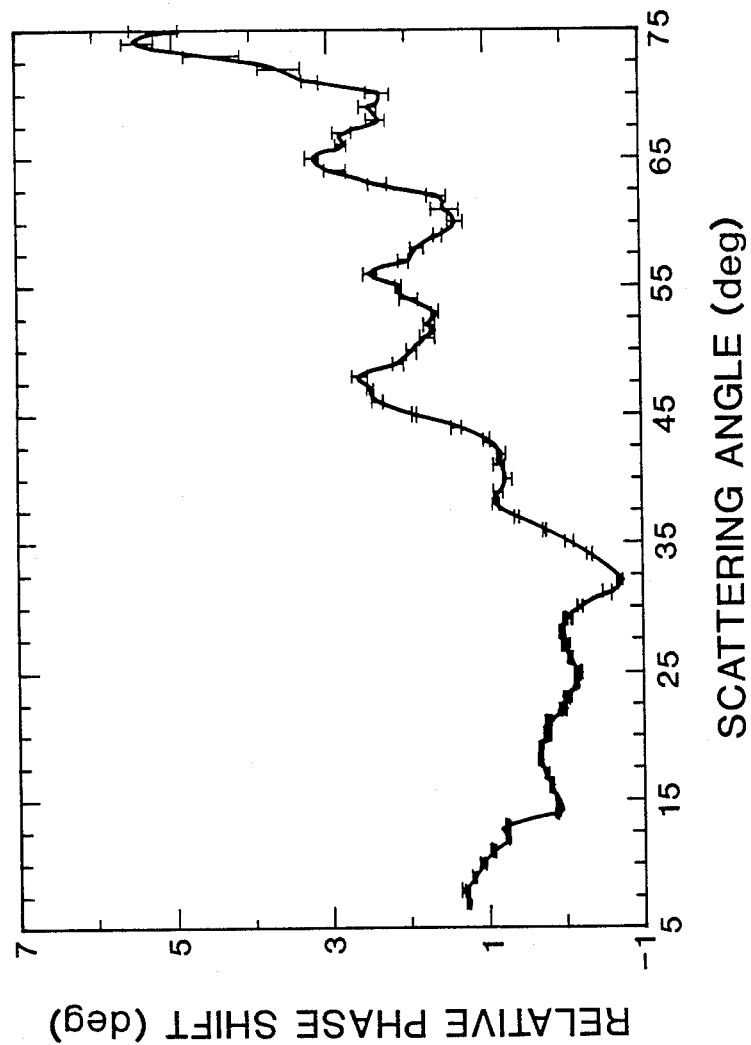
FIG. 10 shows a phase differential scattering spectrum for a human cell sample.
Figure 11:
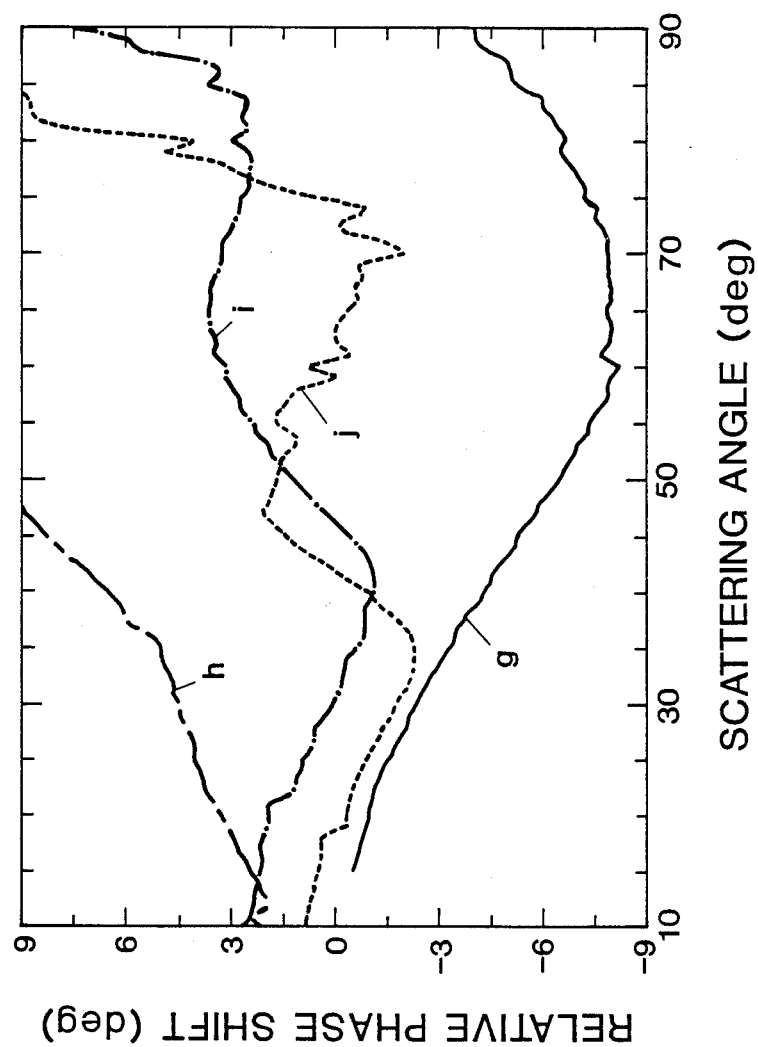
FIG. 11 shows the discrimination between three bacteria and a pollen using phase differnetial scattering.

FIG. 10 shows the phase differential scattering signal for $2\times10^5$ particles/ml of transformed human lymphoblasts, while FIG. 11 shows the scattering signal for three bacterial specimens and a sample of pollen. The scattering volume utilized for the curve in FIG. 10 contained 2800 cells at a scattering angle of 90°, the cells being kept in suspension with the use of a small circulating pump. FIG. 11 at plot 2 represents the signal from $8\times10^7$ particles/ml of *Leptospira biflexa;* FIG. 11 at plot h represents the signal from $3\times10^5$ particles/ml of Paper Mulberry Pollen; FIG. 11 at plot i represents the signal from $9\times10^7$ particles/ml of *Staphylococcus aureus;* and FIG. 11 at plot i represents the signal from $4\times10^7$ particles/ml of *Ecoli luria*.

Figure 12:
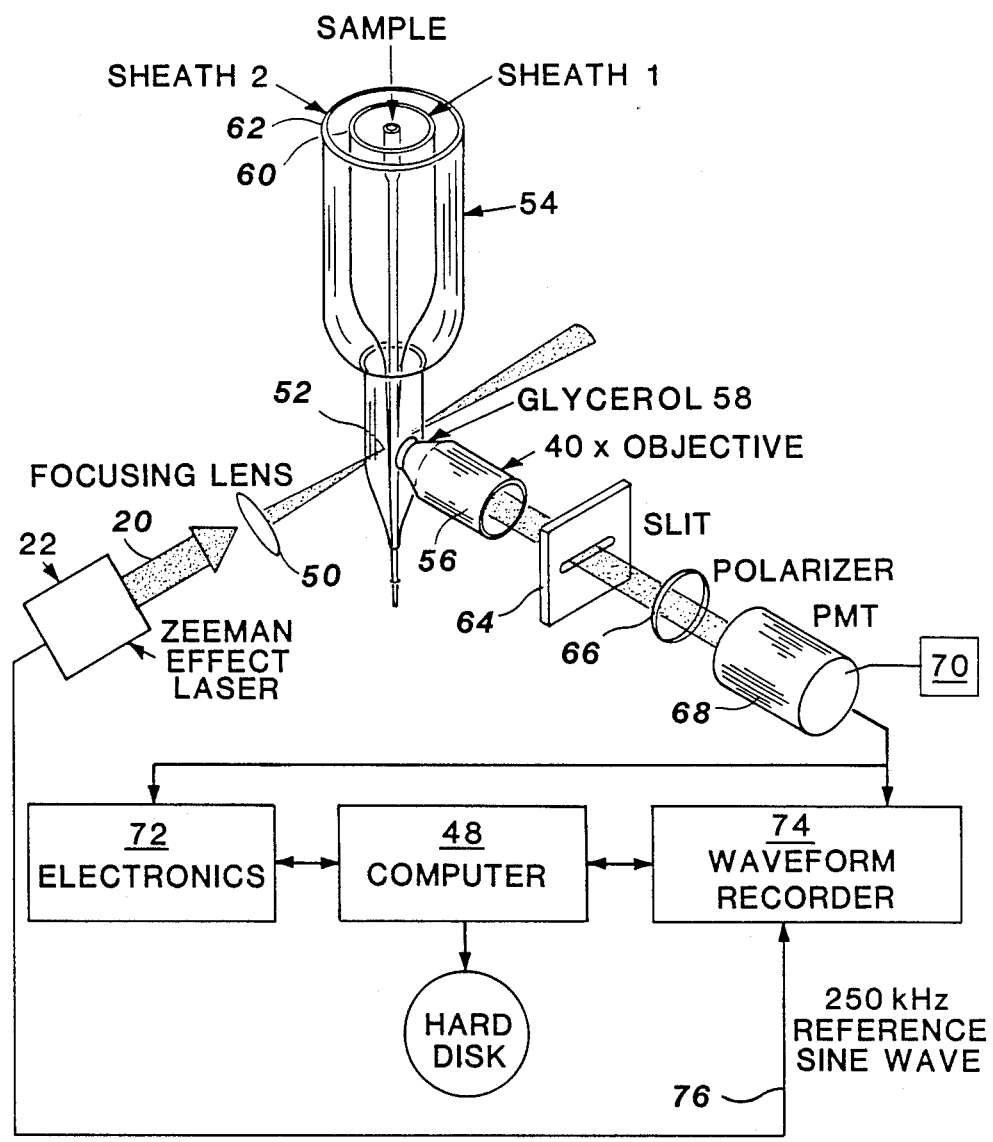
FIG. 12 shows a schematic representation of the apparatus of the present invention being used to make phase differential scattering measurements in a flowing system.

FIG. 12 is a schematic representation of the apparatus used to observe the phase differential scattering signal for a flowing sample. By contrast to the above-described scattering measurements where the scattering signal represents a rotationally averaged orientation effect, particles were analyzed singly in a flowing system and have individual, fixed orientations relative to the incident polarized radiation. Moreover, the emission from the Zeeman effect laser was focused for the flowing measurements. In particular, laser output 20 from Zeeman effect laser 22 is focused by lens 50 to an illumination spot size 52 of about 75 μm within flow cytometer 54. The light scattered at 90° is optically collected by a 40x, 0.75 N.A. objective 56 which is coupled to the flow cytometer chamber using glycerol 58. It was found that for most scatterers a scattering angle of 90° produced a lower amplitude beat frequency than did most other scattering angles. Flow cytometer 54 uses hydrodynamic focusing from two sheath streams 60, 62 to produce an approximately 2 μm diameter sample stream with flow velocity between 1 and 7 μm/μs. Scattered light passing through slit 64 is analyzed by polarizer 66 and detected on photomultiplier 68 which is energized using voltage supply 70. The electrical signal produced thereby is processed by electronics 72 and sent to computer 48. Waveform recorder by line having a 250 kHz reference sine wave introduced thereto by line 76 from within the Zeeman effect laser 22, was also used to observe the phase differential scattering signal from single particles. Waveform recorder 74 captures both the photomultiplier 68 signal and the sine wave reference which is used as a phase reference to determine the phase differential scattering phase shift in the photomultiplier 68 signal.

Figure 13:
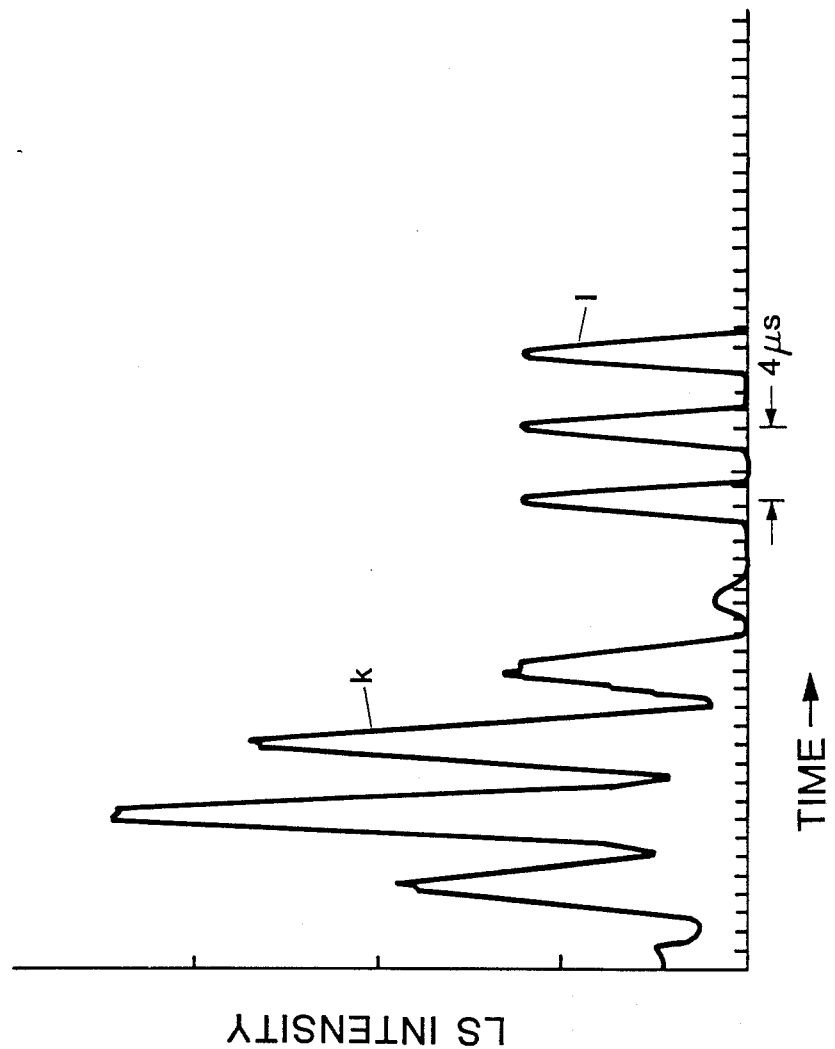
FIG. 13 shows a phase differential scattering measurement for single particles passing through a flow cytometer. Shown is the light scattering intensity as a function of time as a single microsphere doublet traverses a focused Zeeman effect laser beam. The Gaussian envelope of the light scattering is modulated by the 250 kHz beat frequency. A clipped 250 kHz reference sine wave is shown recorded alongside. The relative phase and amplitude of the two waveforms is the information of interest.

FIG. 13 at waveform K shows the recorded phase differential scattering waveform for 90° scattering angle from a single 1.6 μm—1.6 μm microsphere doublet passing through the flow cytometer described in FIG. 12 hereof. The doublet, consisting of two attached 1.6 μm microspheres, is approximately the size of a small human chromosome. The waveform is shown plotted in terms of scattered light intensity as a function of time as the doublet traverses the focused Zeeman effect laser beam. The customary Gaussian pulse shape of the waveform is modulated by the 250 kHz beat frequency of the Zeeman effect laser. It is also possible to record the amplitude and relative phase of the beat frequency as functions of time using analog circuitry, although the waveforms displayed in FIG. 13 were recorded using a waveform recorder. The 250 kHz reference sine wave, which is cut off in the negative direction, is shown in FIG. 13 at waveform 1. In theory, the phase shift in the recorded scattered light waveform can be determined by comparing the phase thereof to that of the simultaneous 250 kHz reference sine wave. This has not yet been achieved quantitatively due to significant phase jitter in the waveform recording process. Finally, it should be pointed out that slit 64 shown in FIG. 12 hereof was not employed in obtaining the curve shown in FIG. 12 at waveform K. However, by using a slit, the spatial resolution of the instrument may be dramatically improved, albeit at the cost of a reduced signal-to-noise ratio of the apparatus.

In summary, the subject invention will not provide complete information about elastic light scattering. This is because combinations of the amplitudes and phases for the amplitude scattering matrix elements are measured and not the amplitudes and phases themselves. In principle, measurements of all of the Mueller scattering matrix elements can provide complete information on the elastic scattering from a sample. As a practical matter, however, complete measurements of the requisite matrix elements can be difficult. Many of these elements represent one part in one thousand or less of the total light scattered by a sample. Furthermore, if the optical components, such as modulators, quarter-wave plates, and polarizers, for example, are imperfect or imperfectly aligned, or if the scattering cell is birefringent, some of the large and relatively uninteresting matrix elements can mix with the smaller matrix elements of interest and mask the information contained therein. Small misalignments or static birefringence in the photoelastic modulators can be troublesome as well. By contrast, phase differential scattering, as described in the present disclosure, has but a single polarizer to align, And, for many measurements contemplated by the inventor, even this alignment is not critical. Approximate corrections for birefringence can be made most easily using the subject apparatus. Phase differential scattering measurements involve measurement of a signal which can have a relatively large amplitude. The beat frequency for some measurements represents up to 50% of the total scattered irradiance at certain scattering angles. Gain instabilities, dc offsets, and noise problems are, therefore, of reduced importance for many phase differential scattering measurements. Phase differential scattering measurements have demonstrated excellent discrimination and reproducibility for various pure pollen and bacterial samples in suspension.

The foregoing description of embodiments of the invention has been presented for purposes of illustration and description. It is not intended to be exhaustive or to limit the invention to the precise form disclosed, and obviously many modifications and variations are possible in light of the above teaching. For example, frequency-stabilized lasers or other electrooptical devices may be used to provide the two frequencies of incident radiation having a constant frequency difference instead of the Zeeman effect laser described hereinabove. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for the indentification and characterization of particles in a sample by observing light scattered therefrom, comprising in combination:
   means for producing a first radiation having a first wavelength and a first polarization;
   means for producing a second radiation substantially collinear with said first radiation and having a second wavelength and a second polarization substantially orthogonal to said first polarization;
   containment means containing said sample, for allowing said first and second radiations to scatter from collisions with said particles in said sample;
   polarization means receiving scattered first and second radiations for resolving said scattered first and second radiations, said polarization means having an axis of transmission along which resolved scattered first and second radiations pass;
   photodetector means receiving and detecting said resolved scattered first and second radiations for outputting a beat frequency resulting from interaction between said resolved scattered first and second radiations, said beat frequency having a relative phase and amplitude; and
   measurement means receiving said beat frequency for measuring and outputting said relative phase of said beat frequency, for use in identifying and characterizing said particles.

2. The apparatus as described in claim 1, further comprising measurement means for measuring and outputting said amplitude of said beat frequency, for use in identifying and characterizing said particles.

3. The apparatus as described in claim 2, further comprising means for moving a combination of said polarization means and said photodetector means about said containment means to measure and output said relative phase and said amplitude of said beat frequency as functions of scattering angle.

4. The apparatus as described in claim 1, further comprising means located intermediate said containment means and said photodetector means for defining the volume of said scattered first and second radiations.

5. The apparatus as described in claim 1, wherein said first polarization and said second polarization comprise linear polarizations.

6. The apparatus as descried in claim 5, wherein the angle of said axis of transmission of said polarization means with respect to the axis of said first polarization is selected from the group comprising 0°, 45°, and 90°.

7. The apparatus as described in claim 1, wherein said means for producing a first radiation and said means for producing a second radiation comprise laser means.

8. The apparatus as described in claim 7, wherein said first and second radiations have a difference frequency of not more than 100 MHz.

9. The apparatus as described in claim 8, wherein said difference frequency is stable to at least 0.1 parts per million.

10. The apparatus as described in claim 7, wherein said laser means comprises a two-frequency Zeeman effect laser.

11. The apparatus as described in claim 1, wherein said first polarization and said second polarization comprise circular polarizations.

12. The apparatus as described in claim 11, wherein said polarization means includes a circular polarizer.

13. A method for identifying and characterizing particles in a sample by observing light scattered therefrom, which comprises the steps of:
   producing a first radiation having a first wavelength and a first polarization;
   producing a second radiation substantially collinear with said first radiation and having a second wavelength and a second polarization substantially orthogonal to said first polarization;
   scattering said first and second radiations by irradiating said sample with said first and second radiations;
   receiving and resolving scattered first and second radiations along an axis of transmission having a predetermined polarization angle, and outputting resolved scattered first and second radiations;
   detecting said resolved scattered first and second radiations, said detection producing a beat frequency, having a relative phase and amplitude, from the interaction of said resolved scattered first radiation with said resolved scattered second radiation, and outputting said beat frequency;
   measuring said relative phase of said beat frequency; and
   outputting said relative phase for use in identifying and characterizing said particles.

14. The method as described in claim 13, further comprising the steps of measuring and outputting said amplitude of said beat frequency.

15. The method as described in claim 14, further comprising the steps of measuring said relative phase and said amplitude of said beat frequency at a plurality of scattering angles, and outputting said relative phase and said amplitude of said beat frequency as functions of said plurality of scattering angles.

16. The method as described in claim 13, further comprising the step of defining the volume of said scattering first and second radiations after the step of scattering said first and second radiations, and again after the step of outputting resolved scattered first and second radiations.

17. The method as described in claim 13, wherein said first and second radiations comprise laser radiations.

18. The method as described in claim 17, wherein the difference frequency between said first wavelength and said second wavelength is not more than 100 MHz.

19. The method as described in claim 18, wherein said difference frequency is stable to at least 0.1 parts per million.

20. The method as described in claim 17, wherein said laser radiations comprise two-frequency Zeeman effect laser radiations.

21. The method as described in claim 13, wherein said first polarization and said second polarization comprise linear polarizations.

22. The method as described in claim 21, wherein said predetermined polarization angle with respect to the axis of said first polarization is from the group comprising 0°, 45°, and 90°.

23. The method as described in claim 13, wherein said first polarization and said second polarization comprise circular polarizations;

24. The method as described in claim 23, wherein said step of receiving and resolving said scattered first and second radiations includes resolving said scattered first and second radiation into circularly polarized scattered first and second radiations.

25. Apparatus for the indentification and characterization of individual particles in a flow by observing light scattered therefrom, comprising in combination;

means for producing a first radiation having a first wavelength and a first polarization;

means for producing a second radiation substantially collinear with said first radiation and having a second wavelength and a second polarization substantially orthogonal to said first polarization;

containment means controlling the flow of said individual particles for allowing said first and second wavelengths to scatter from collisions with said individual particles;

polarization means receiving scattered first and second radiations for resolving said scattered first and second radiations, said polarization means having an axis of transmission along which resolved scattered first and second radiations pass;

photodetector means receiving and detecting said resolved scattered first and second radiations for outputting the beat frequency resulting from the interaction between said resolved scattered first and second radiations, said beat frequency having a relative phase and amplitude; and measurement means receiving said beat frequency for measuring and outputting said relative phase as a function of time for use in identifying and characterizing said individual particles.

26. The apparatus as described in claim 25, further comprising means for measuring and outputting said amplitude of said beat frequency as a function of time for use in identifying and characterizing said individual particles.

27. The apparatus as described in claim 26, further comprising means for measuring and outputting said relative phase and said amplitude of said beat frequency as functions of time at a plurality of scattering angles.

28. The apparatus as described in claim 25, wherein said means for producing said first and second radiations comprise laser means.

29. The apparatus as described in claim 24, wherein said first and second radiations have a difference frequency of no more than 100 MHz.

30. The apparatus as described in claim 29, wherein said difference frequency is stable to at least 0.1 parts per million.

31. The apparatus as described in claim 28, wherein said laser means comprises a two-frequency Zeeman effect laser.

32. The apparatus as described in claim 25, wherein said first polarization and said second polarization comprise linear polarizations.

33. The apparatus as described in claim 32, wherein the angle of said axis of transmission of said polarization means with respect to the axis of said first polarization is selected from the group comprising 0°, 45°, and 90°.

34. The apparatus as described in claim 25, wherein said first polarization and said second polarization comprise circular polarizations.

35. The apparatus as described in claim 34, wherein said polarization means comprises a circular polarizer.

36. The apparatus as described in claim 25, further comprising focusing means for reducing the diameter of said first and second radiations prior to collision with said individual particles.

37. The apparatus as described in claim 25, further comprising light gathering means intermediate of said containment means and said polarization means for maximizing collection of said scattered first and second radiations.

38. The apparatus as described in claim 25, further comprising slit means intermediate of said containment means and said polarization means, for improving spatial resolution of said scattered first and second radiations.

39. A method for identifying and characterizing individual particles in a flow by observing light scattered therefrom, comprising the steps of:

producing a first radiation having a first wavelength and a first polarization;

producing a second radiation substantially collinear with said first radiation and having a second wavelength and a second polarization substantially orthogonal to said first polarization;

scattering said first and second radiations by irradiating said particles in a flow with said first and second radiations;

receiving and resolving scattered first and second radiations along an axis of transmission having a predetermined polarization angle, and outputting resolved scattered first and second radiatons;

detecting said resolved scattered first and second radiations, said detection producing a beat frequency, having a relative phase and amplitude, from the interaction of said resolved scattered first radiation with said resolved scattered second radiation, and outputting said beat frequency;

measuring said relative phase of said beat frequency as function of time; and outputting said relative phase of said beating frequency as a function of time for use in identifying and characterizing said individual particles.

40. The method as described in claim 39, further comprising the steps of measuring and outputting said amplitude of said beat frequency as a function of time for use in identifying and characterizing said individual particles.

41. The method as described in claim 40, further comprising the step of measuring said relative phase and said amplitude as functions of time at a plurality of scattering angles, and outputting said relative phase and said amplitude as functions of time and of said scattering angles.

42. The method as described in claim 39, wherein said first polarization and said second polarization comprise linear polarizations.

43. The method as described in claim 42, wherein said predetermined polarization angle with respect to the axis of said first polarization is chosen from the group comprising 0°, 45°, and 90°.

44. The method as described in claim 39, wherein said first and second radiations comprise laser radiations.

45. The method as described in claim 44, wherein the difference frequency between said first wavelength and said second wavelength is not more than 100 MHz.

46. The method as described in claim 45, wherein said difference frequency is stable to at least 0.1 parts per million.

47. The method as described in claim 44, wherein said laser radiations comprise two-frequency Zeeman effect laser radiations.

48. The method as described in claim 39, wherein said first polarization and said second polarization comprise circular polarizations.

49. The method as described in claim 48, wherein said step of receiving and resolving said scattered first and second radiations further comprises resolving said scattered first and second radiations into circularly polarized scattered first and second radiations.

50. The method as described in claim 39, further comprising the step of reducing the beam diameter of said first and second radiations before being scattered by said particles in a flow.

51. The method as described in claim 39, further comprising the step of optically collecting said scattered first and second radiations before said step of receiving and resolving said scattered first and second radiations.

* * * * *